United States Patent
Meglan

(10) Patent No.: US 12,029,517 B2
(45) Date of Patent: Jul. 9, 2024

(54) SYSTEMS, METHODS, AND COMPUTER-READABLE MEDIA FOR DETECTING IMAGE DEGRADATION DURING SURGICAL PROCEDURES

(71) Applicant: Covidien LP, Mansfield, MA (US)

(72) Inventor: Dwight Meglan, Westwood, MA (US)

(73) Assignee: Covidien LP, Mansfield, MA (US)

( * ) Notice: Subject to any disclaimer, the term of this patent is extended or adjusted under 35 U.S.C. 154(b) by 15 days.

(21) Appl. No.: 17/941,053

(22) Filed: Sep. 9, 2022

(65) Prior Publication Data
US 2023/0005150 A1    Jan. 5, 2023

Related U.S. Application Data

(63) Continuation of application No. 17/256,422, filed as application No. PCT/US2019/038869 on Jun. 25, 2019, now Pat. No. 11,576,739.

(Continued)

(51) Int. Cl.
A61B 34/37    (2016.01)
A61B 1/00    (2006.01)
(Continued)

(52) U.S. Cl.
CPC .......... *A61B 34/37* (2016.02); *A61B 1/00009* (2013.01); *A61B 1/00193* (2013.01);
(Continued)

(58) Field of Classification Search
CPC . A61B 34/37; A61B 1/00009; A61B 1/00193; A61B 34/30; A61B 2034/302;
(Continued)

(56) References Cited

U.S. PATENT DOCUMENTS 6,069,691 A    5/2000    Rosow et al.
6,132,368 A    10/2000    Cooper
(Continued)

FOREIGN PATENT DOCUMENTS

CN    106204523 A    12/2016
WO    2020009830 A1    1/2020

OTHER PUBLICATIONS

International Search Report mailed Oct. 15, 2019 and Written Opinion completed Oct. 15, 2019 corresponding to counterpart Int'l Patent Application PCT/US2019/038869.
(Continued)

*Primary Examiner* — Loi H Tran
(74) *Attorney, Agent, or Firm* — Carter, DeLuca & Farrell LLP

(57) ABSTRACT

Methods, systems, and computer-readable media for detecting image degradation during a surgical procedure are provided. A method includes receiving images of a surgical instrument; obtaining baseline images of an edge of the surgical instrument; comparing a characteristic of the images of the surgical instrument to a characteristic of the baseline images of the edge of the surgical instrument, the images of the surgical instrument being received subsequent to obtaining the baseline images of the edge of the surgical instrument and being received while the surgical instrument is disposed at a surgical site in a patient; determining whether the images of the surgical instrument are degraded, based on the comparing of the characteristic of the images of the surgical instrument and the characteristic of the baseline images of the surgical instrument; and generating an image degradation notification, in response to a determination that the images of the surgical instrument are degraded.

20 Claims, 5 Drawing Sheets

Related U.S. Application Data

(60) Provisional application No. 62/693,530, filed on Jul. 3, 2018.

(51) Int. Cl.
*G06T 7/00* (2017.01)
*H04N 13/204* (2018.01)
*A61B 34/30* (2016.01)

(52) U.S. Cl.
CPC ......... *G06T 7/0014* (2013.01); *H04N 13/204* (2018.05); *A61B 34/30* (2016.02); *G06T 2207/10012* (2013.01); *G06T 2207/10068* (2013.01); *G06T 2207/30168* (2013.01)

(58) Field of Classification Search
CPC .. A61B 2017/00725; A61B 2090/0807; A61B 2090/3937; A61B 90/94; A61B 34/74; A61B 2090/081; A61B 2090/371; G06T 7/0014; G06T 2207/10012; G06T 2207/10068; G06T 2207/30168; G06T 7/0002; G06T 2207/30068; H04N 13/204
USPC ......................................................... 348/45
See application file for complete search history.

(56) References Cited

U.S. PATENT DOCUMENTS

| | | |
|---|---|---|
| 6,206,903 B1 | 3/2001 | Ramans |
| 6,219,182 B1 | 4/2001 | McKinley |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,388,742 B1 | 5/2002 | Duckett |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,189,000 B2 | 3/2007 | Miyauchi et al. |
| 7,239,940 B2 | 7/2007 | Wang et al. |
| 7,277,120 B2 | 10/2007 | Gere et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, II et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,223,193 B2 | 7/2012 | Zhao et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |

(56) References Cited

U.S. PATENT DOCUMENTS

| | | |
|---|---|---|
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,939,894 B2 | 1/2015 | Morrissette et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,134,150 B2 * | 9/2015 | Zhao .................... H04N 13/246 |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,526,587 B2 * | 12/2016 | Zhao .................... A61B 34/37 |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |

(56) References Cited

U.S. PATENT DOCUMENTS

| | | |
|---|---|---|
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,576,739 B2 | 2/2023 | Meglan |
| 2003/0007672 A1 | 1/2003 | Harman et al. |
| 2004/0159773 A1* | 8/2004 | Fein ................ G01N 21/6458 250/208.1 |
| 2007/0156021 A1 | 7/2007 | Morse et al. |
| 2011/0301447 A1 | 12/2011 | Park et al. |
| 2016/0117823 A1 | 4/2016 | Isaacs et al. |
| 2016/0210518 A1* | 7/2016 | Script ............ G08B 13/19665 |
| 2018/0168737 A1 | 6/2018 | Ren |
| 2019/0378301 A1* | 12/2019 | Lee .................. H04N 13/204 |

OTHER PUBLICATIONS

International Search Report dated Oct. 15, 2019 and Written Opinion completed Oct. 15, 2019 corresponding to counterpart Int'l Patent Application PCT/US2019/038869.

Extended European Search Report dated Mar. 22, 2022 corresponding to counterpart Patent Application EP 19829924.0.

* cited by examiner

SYSTEMS, METHODS, AND COMPUTER-READABLE MEDIA FOR DETECTING IMAGE DEGRADATION DURING SURGICAL PROCEDURES

CROSS-REFERENCE TO RELATED APPLICATIONS

The present application is a Continuation of U.S. patent application Ser. No. 17/256,422, filed Dec. 28, 2020, which is a U.S. National Stage Application filed under 35 U.S.C. § 371(a) of International Patent Application Serial No. PCT/US2019/038869, filed Jun. 25, 2019, which claims the benefit of and priority to U.S. Provisional Patent Application Ser. No. 62/693,530, filed Jul. 3, 2018, the entire disclosure of each of which is incorporated by reference herein.

BACKGROUND

Robotic surgical systems may be used in minimally invasive surgical procedures. During a robotic surgical procedure, a surgeon controls a robotic surgical arm with a user interface at a remote surgeon console. The user interface allows the surgeon to manipulate a surgical instrument coupled to the robotic arm and to control a camera to receive images of a surgical site within a patient.

The surgeon console may include a stereoscopic display, sometimes referred to as a three-dimensional (3D) display. In this regard, sometimes in conjunction with a corresponding pair of stereoscopic eyeglasses worn by the surgeon, such displays facilitate depth perception from an image by presenting the image to the surgeon as a pair of distinct images separately provided to the left and right eyes, respectively. The stereoscopic display may display images provided by a stereoscopic endoscope. Stereoscopic endoscopes employ two signal paths, usually a left-eye view and a right-eye view, which are matched and interdigitated to generate a stereoscopic image. As does typically occur during surgical procedures, biological material or other procedure-related material may occlude one of the lenses of the stereoscopic endoscope, thereby degrading the images provided to the display. In the case of a stereoscopic endoscope, this degradation has potential side effects upon the surgeon through the now mismatched stereoscopic image pairs which can cause perception issues that tax the surgeon's visual and cognitive pathways without the surgeon's awareness. This can result in degraded performance of the surgeon in perceiving and responding to the observed stereoscopic information. Thus, it is useful to be able to detect these mismatch situations and inform the surgeon of the need to correct the situation.

SUMMARY

Disclosed according to embodiments of the present disclosure are methods for detecting image degradation during a surgical procedure. In an aspect of the present disclosure, an illustrative method includes receiving images of a surgical instrument, obtaining baseline images of an edge of the surgical instrument, comparing a characteristic of the images of the surgical instrument to a characteristic of the baseline images of the edge of the surgical instrument, the images of the surgical instrument being received subsequent to the obtaining of the baseline images of the edge of the surgical instrument and being received while the surgical instrument is disposed at a surgical site in a patient, determining whether the images of the surgical instrument are degraded, based on the comparing of the characteristic of the images of the surgical instrument and the characteristic of the baseline images of the edge of the surgical instrument, and generating an image degradation notification, in response to a determination that the images of the surgical instrument are degraded.

In a further aspect of the present disclosure, the images of the surgical instrument are received by an image capture device.

In another aspect of the present disclosure, the image capture device is a stereoscopic endoscope including a left-eye lens and a right-eye lens.

In a further aspect of the present disclosure, the characteristic of the baseline images of the edge of the surgical instrument is obtained during an initial image capture device calibration.

In a further aspect of the present disclosure, the method further includes periodically receiving images of the edge of the surgical instrument at a predetermined interval.

In another aspect of the present disclosure, the determination that the images of the surgical instrument are degraded is based at least in part on a difference between the characteristic of the received images of the surgical instrument and the characteristic of the baseline images of the edge of the surgical instrument being greater than a threshold value.

In yet another aspect, the method further includes determining the characteristic of the images of the surgical instrument by computing a modulation transfer function derived from the received images of the surgical instrument.

Disclosed according to embodiments of the present disclosure are systems for detecting image degradation during a surgical procedure. In an aspect of the present disclosure, an illustrative system includes a surgical instrument including at least one edge, an image capture device configured to capture images of the surgical instrument, the images of the surgical instrument including a characteristic, a display device, at least one processor coupled to the image capture device and the display device, and a memory coupled to the at least one processor and having stored thereon a characteristic of baseline images of the edge of the surgical instrument, and instructions which, when executed by the at least one processor, cause the at least one processor to obtain the characteristic of the baseline images of the edge of the surgical instrument, receive the images of the surgical instrument, compare a characteristic of the images of the surgical instrument to the characteristic of the baseline images of the edge of the surgical instrument, the images of the surgical instrument being received subsequent to the obtaining of the characteristic of the baseline images of the edge of the surgical instrument and being received while the surgical instrument is disposed at a surgical site in a patient, determine whether the images of the surgical instrument are degraded, based on the comparing of the characteristic of the images of the surgical instrument and the characteristic of the baseline images of the edge of the surgical instrument, and generate an image degradation notification, in response to a determination that the images of the surgical instrument are degraded.

Disclosed according to embodiments of the present disclosure are non-transitory computer-readable media storing instructions for detecting image degradation during a surgical procedure. In an aspect of the present disclosure, an illustrative non-transitory computer-readable medium stores instructions which, when executed by a processor, cause the processor to receive images of a surgical instrument, obtain baseline images of an edge of the surgical instrument, compare a characteristic of the images of the surgical instrument to a characteristic of the baseline images of the edge of the surgical instrument, the images of the surgical instrument being received subsequent to obtaining the baseline images of the edge of the surgical instrument and being received while the surgical instrument is disposed at a surgical site in a patient, determine whether the images of the surgical instrument are degraded, based on the comparison of the characteristic of the images of the surgical instrument and the characteristic of the baseline images of the edge of the surgical instrument, and generate an image degradation notification, in response to a determination that the images of the surgical instrument are degraded.

Any of the above aspects and embodiments of the present disclosure may be combined without departing from the scope of the present disclosure.

BRIEF DESCRIPTION OF THE DRAWINGS

Objects and features of the presently disclosed systems, methods, and computer-readable media will become apparent to those of ordinary skill in the art when descriptions of various embodiments thereof are read with reference to the accompanying drawings, wherein.

DETAILED DESCRIPTION

Figure 1:
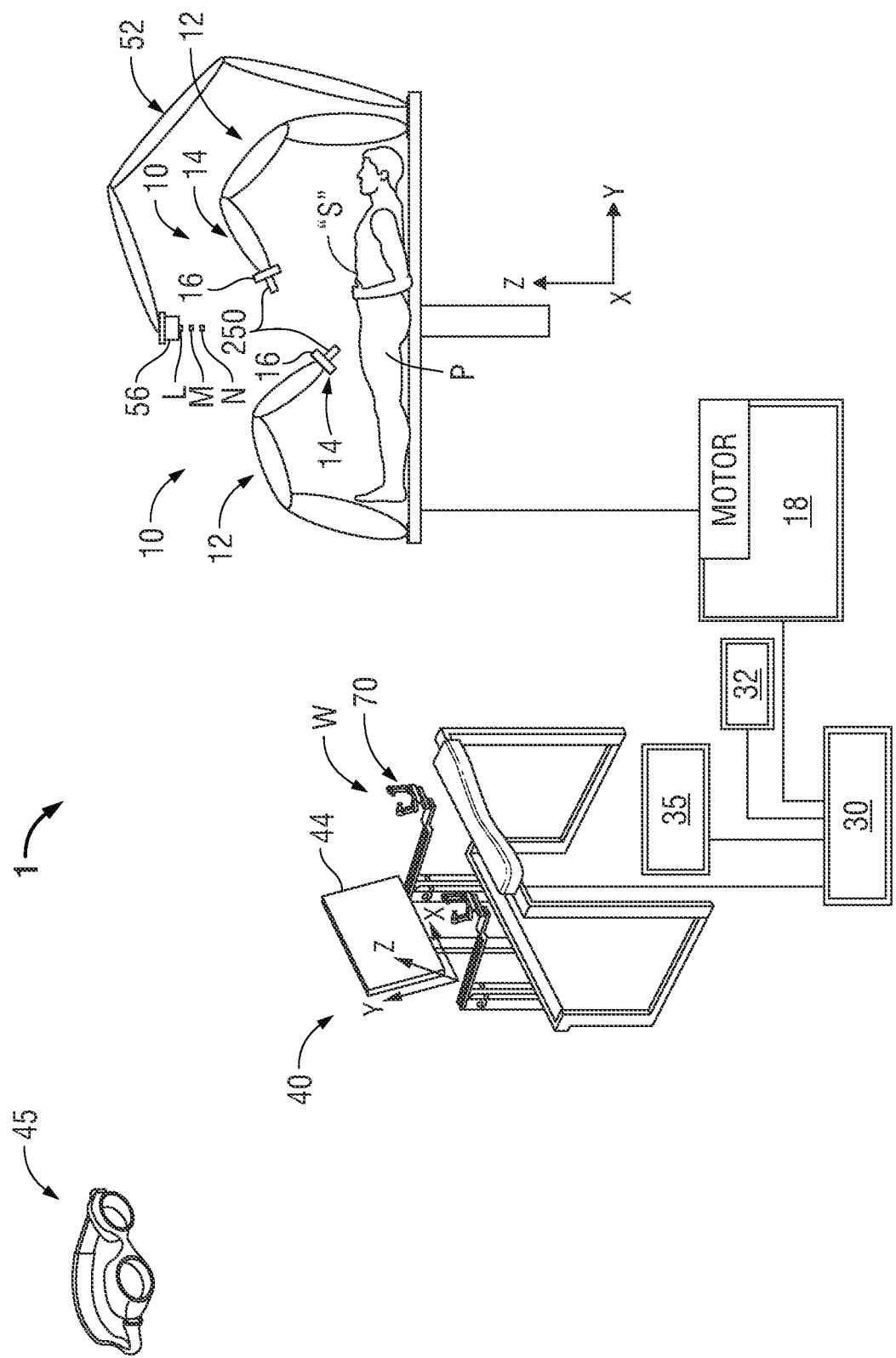
FIG. 1 is a schematic diagram of a robotic surgical system, in accordance with embodiments of the present disclosure.

The present disclosure generally relates to dynamic detection of image degradation, and providing associated notifications, during a surgical procedure. In order to determine an amount of degradation occurring during a surgical procedure, endoscopic calibration techniques may be used. Prior to its use, and/or at the start of a surgical procedure, an endoscopic imaging system may be calibrated. Calibration, prior to use, includes the process of determining and recording base parameters, at peak or near-peak operating conditions for the imaging system by using a calibration target. Calibration prior to the use of the endoscopic system thus provides a baseline metric of the endoscopic system before the occurrence of degradation. During a surgical procedure, a similar technique as that employed during calibration may be used to determine current parameters of the endoscopic imaging system. By automatically and dynamically comparing the current parameters with those of the base parameters, endoscopic image degradation can be determined.

To that end, the present disclosure relates to systems, methods, and computer-readable media for enabling dynamic detection of image degradation of images of a surgical site during a surgical procedure, and for generating and displaying image degradation notifications during the surgical procedure. In this regard, during calibration of the image capture device, one or more baseline parameters of the image capture device, based on calibration targets such as test patterns and/or edges of tools within the image capture device's field of view, are determined and recorded. During the surgical procedure, images of the surgical site are captured by the image capture device and provided to a computing device, such as a control console, for processing, using a similar technique as that employed during calibration, to determine one or more current parameters of the image capture device. By dynamically comparing the current parameter(s) with the baseline parameter(s) of the image capture device, a determination regarding image degradation can be made.

As used herein, the terms "clinician," "surgeon," "observer," and/or "viewer" generally refer to a user of a stereoscopic display device described herein. Additionally, although the terms "first eye" and "second eye" are used herein to refer to a left eye and a right eye, respectively, of a user, this use is provided by way of example and should not be construed as limiting. Throughout this description, the term "proximal" refers to the portion of the device or component thereof that is farthest away from the patient (and thus closest to the clinician and/or surgical robot) and the term "distal" refers to the portion of the device or component thereof that is closest to the patient (and thus furthest away from the clinician and/or surgical robot). Further, as referred herein, the term "signal path" (whether right-eye or left-eye) refers to an optical-electrical-optical signal path whereby images are captured optically, converted to an electrical/digital signal to be transmitted, and again converted back to an optical image when received by a computing or display device. While the illustrative embodiments below describe a robotic surgical system, those skilled in the art will recognize that the systems, methods, and computer-readable media described herein may also be used in other surgical procedures, for example minimally-invasive surgical procedures, where a patient image capture device is used to capture images of a surgical site. Thus, the present disclosure is not intended to be limited to the exemplary embodiments using a robotic surgical system, as described hereinbelow.

Figure 3:
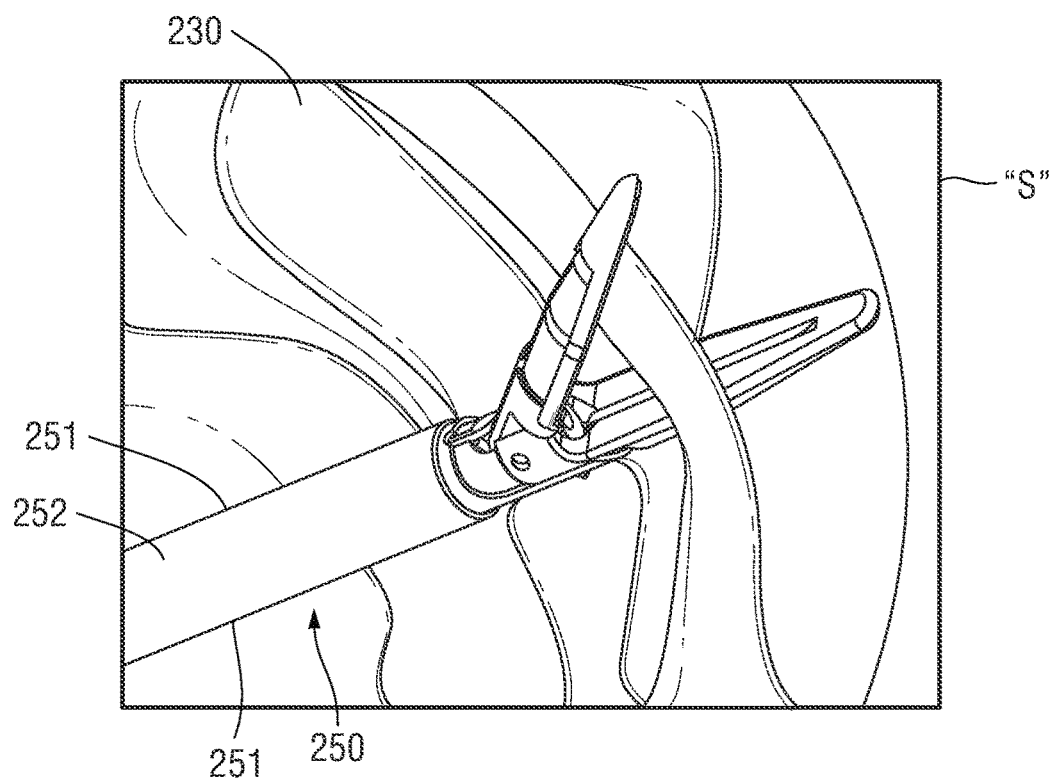
FIG. 3 is an image of a surgical site received from an image capture device, in accordance with the present disclosure.

With reference to FIG. 1, a robotic surgical system 1 is illustrated, and generally includes a surgical robot 10, a controller 30, at least one processor 32, at least one memory 35, and a user interface console 40. Surgical robot 10 generally includes one or more robotic arms 12 and a base 18. Robotic arms 12 may be in the form of arms or linkages each having an end 14 that supports a surgical instrument 250. Surgical instrument 250 may be any type of instrument usable with robotic arm 12, such as a grasper, a knife, scissors, staplers, and/or the like. One or more of robotic arms 12 may include an imaging device 16 for imaging a surgical site "S," as also shown in FIG. 3.

Controller 30 includes, and/or is communicatively coupled to, the at least one processor 32 and memory 35, and may be integrated with user interface 40 or provided as a standalone device within the operating theater. As described in further detail below, processor 32 executes instructions (not shown) stored in memory 35 to perform steps and/or procedures of the various embodiments described herein. As will be appreciated, the implementation of processor 32 and memory 35 is provided by way of example only and should not be construed as limiting. For instance, steps and/or procedures of any of the embodiments of the present disclosure may be implemented by hardware components, firmware components, software components, and/or any combination thereof.

User interface 40 communicates with base 18 through controller 30 and includes a display device 44 which is configured to display stereoscopic images of the surgical site "S." The images are captured by an imaging device (also referred to as "image capture device") 16 and/or captured by imaging devices that are positioned about the surgical theater (e.g., an imaging device positioned adjacent patient "P," and/or an imaging device 56 positioned at a distal end of an imaging arm 52). Imaging devices (e.g., imaging devices 16, 56) may capture optical images, infra-red images, ultrasound images, X-ray images, thermal images, and/or any other known real-time images of surgical site "S." Imaging devices 16, 56 transmit captured images to controller 30 for processing, such as by processor 32, and transmits the captured and/or processed images to display device 44 for display. In one embodiment, one or both of imaging devices 16, 56 are stereoscopic endoscopes capable of capturing images of surgical site "S" via a right-eye lens 210 and a left-eye lens 220, as further described in the description of FIG. 2.

In further embodiments, user interface 40 may include or be associated with a portable display device 45, which, similar to display device 44, is configured to permit the user to view the stereoscopic images in a manner that the user perceives a three-dimensional and/or depth effect from the stereoscopic images. Portable display device 45 may be goggles, glasses, or any other portable or semi-portable display device, which may be used to allow the user to view stereoscopic images.

User interface 40 further includes input handles attached to gimbals 70 which allow a clinician to manipulate surgical robot 10 (e.g., move robotic arms 12, ends 14 of robotic arms 12, and/or surgical instrument 250). Each of gimbals 70 is in communication with controller 30 and processor 32 to transmit control signals thereto and to receive feedback signals therefrom. Additionally or alternatively, each of gimbals 70 may include control interfaces or input devices (not shown) which allow the surgeon to manipulate (e.g., clamp, grasp, fire, open, close, rotate, thrust, slice, etc.) surgical instrument 250 supported at ends 14 of robotic arms 12.

Each of gimbals 70 is moveable to move ends 14 of robotic arms 12 within surgical site "S." The stereoscopic images displayed on display device 44 are oriented such that movement of gimbals 70 moves ends 14 of robotic arms 12 as viewed on display device 44. It will be appreciated that the orientation of the stereoscopic images on display device 44 may be mirrored or rotated relative to a view from above patient "P." In addition, it will be appreciated that the size of the stereoscopic images displayed on display device 44 may be scaled to be larger or smaller than the actual structures of surgical site "S" permitting the surgeon to have a better view of structures within surgical site "S." As gimbal 70 is moved, surgical instrument 250 are moved within surgical site "S." Movement of surgical instrument 250 may also include movement of ends 14 of robotic arms 12 which support surgical instrument 250. In addition to gimbals 70, one or more additional input devices may be included as part of user interface 40, such as a handle including a clutch switch, a touchpad, joystick, keyboard, mouse, or other computer accessory, and/or a foot switch, pedal, trackball, or other actuatable device configured to translate physical movement from the clinician into signals sent to processor 32.

As noted briefly above, to provide the user with a view of surgical site "S" during a surgical procedure, one or more of imaging devices 16, 56 may be a stereoscopic endoscope disposed about surgical site "S," such as adjacent to surgical instrument 250, and configured to capture images of surgical site "S" to be displayed as stereoscopic images on display device 44.

Figure 2:
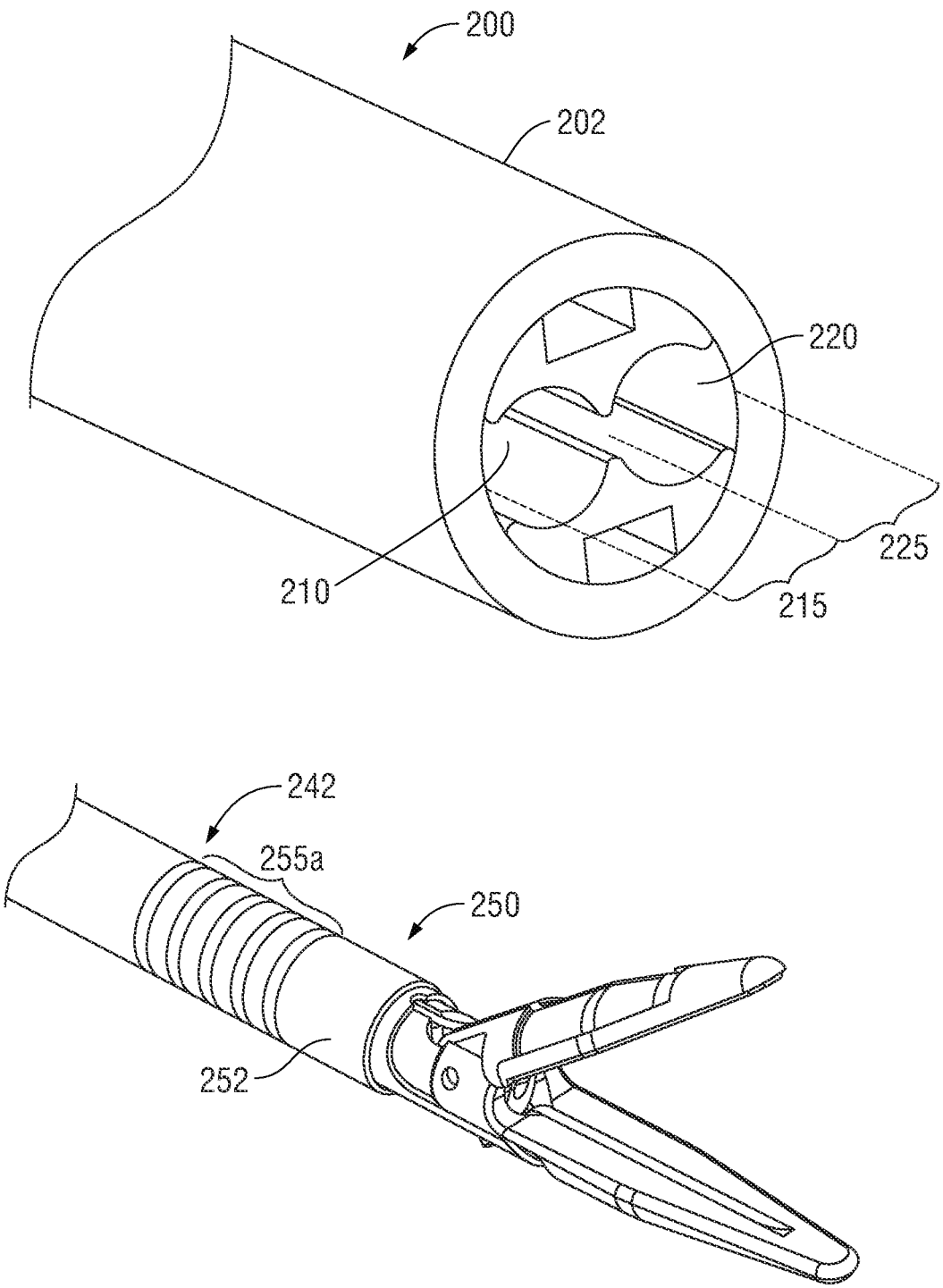
FIG. 2 is a simplified perspective view of an image capture device and a surgical instrument, in accordance with embodiments of the present disclosure.

Turning now to FIG. 2, a simplified, perspective view of a distal end of image capture device 200, such as imaging devices 16, 56, and a distal end of surgical instrument 250 are provided, in accordance with an embodiment of the present disclosure. Image capture device 200 captures images of surgical site "S" via right-eye lens 210 and left-eye lens 220 to provide two distinct view point images that are transmitted to processor 32 for processing, and to display device 44 for display. Image capture device 200 includes a body 202, which includes, at its distal end, a lens assembly including right-eye lens 210 and left-eye lens 220. Right-eye lens 210 and left-eye lens 220 are each associated with a respective right-eye signal path and a left-eye signal path to provide the captured images of surgical site "S" to processor 32 and display device 44.

Surgical instrument 250 is illustrated as a vessel sealing device, which includes a body 242 having a surface 252. Those skilled in the art will recognize that this illustrative surgical instrument 250 is provided merely as an example, and that any other surgical tool or device may be substituted for the illustrated vessel sealing device without departing from the scope of the present disclosure. In some embodiments, one or more test patterns (for example, test pattern 255a) are included on surgical instrument 250. The test pattern is an identifier, for example a unique identifier, that can be used to distinguish surgical instrument 250 from a background during image processing. For example, as depicted in FIG. 2, test pattern 255a is disposed on surface 252 of surgical instrument 250 and may be black and white alternating solid bars. In other embodiments, the test pattern may be any pattern, shapes, colors, or design providing contrast to be used in the detection of degradation of lenses 210, 220 of image capture device 200 and/or of images captured by image capture device 200.

Figure 5:
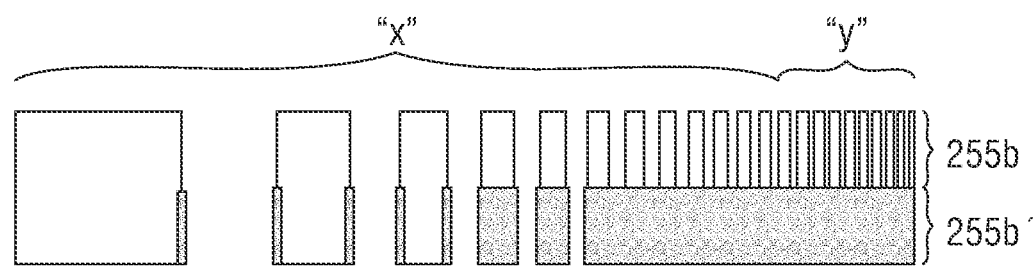
FIG. 5 shows images of a test patterns which may be disposed on a surgical instrument, in accordance with another embodiment of the present disclosure.

In another embodiment, as shown in FIG. 5, test pattern 255b may be made up of increasingly thinner alternating solid black and white bars. Using such a pattern permits image capture device 200 to distinguish between where a black bar ends and a white bar begins. For example, and as described in greater detail in the description of FIG. 5, as the bars become thinner from one end of test pattern 255b to the other, the distinction between the bars becomes increasingly more difficult to detect. In still another embodiment, the test pattern is a passive test pattern, which is not detectable by the user during a surgical procedure. For example, the passive test pattern may be disposed on surface 252 of surgical instrument 250 in a manner that reflects light in an infrared or ultraviolet range.

In still another embodiment, test patterns 255a, 255b extend along an entire outer area of surface 252 of surgical instrument 250. Alternatively, it is contemplated that test patterns 255a, 255b may be located at discrete locations on surface 252 of surgical instrument 250. In a further embodiment, it is contemplated that any of test patterns 255a, 255b may include specific markers, such as specialized shapes, which enhance the ability of image capture device 200 to determine that test patterns 255a, 255b are present within the received image of surgical site "S." In embodiments, it is contemplated that test patterns 255a, 255b correspond to a type of surgical instrument so that each different surgical instrument 250 or type of surgical instrument 250 (for example, ablation device, dissection device, stapler, vessel sealing device, etc.) has a unique test pattern, which can be used to, where necessary, identify surgical instrument 250.

In still another embodiment, a pseudo test pattern is generated using a contrast between surgical instrument 250 and the background of an image of surgical instrument 250. The pseudo test pattern may be a proxy or substitute for an actual test pattern, such as test pattern 255a, 255b. In some embodiments, one or more geometric characteristics of surgical instrument 250 may be used as a pseudo test pattern and/or may be used to define a region of an image that acts as a pseudo test pattern. In one illustrative embodiment, one or more edges of surgical tool 250 are used to define a pseudo test pattern, e.g., the regions of the image on both sides of an edge of surgical tool 250 define a pseudo test pattern. For example, referring now to FIG. 3, image capture device 200 (not shown), using lenses 210, 220 continually captures images of surgical site "S." Surgical site "S" includes anatomical material 230, which may include tissue, bone, blood vessels, and/or other biological material, and surgical instrument 250, which includes edges 251, is positioned within surgical site "S." Although shown as a single image, each of right-eye lens 210 and left-eye lens 220 captures a different image of surgical site "S," which is displayed by display device 44 as a stereoscopic image of surgical site "S." As briefly alluded to above, test patterns need not be disposed on surface 252 of surgical instrument 250. Rather, a pseudo test pattern 255c may be created by the differences in luminance between surgical instrument 250 extending to edges 251 and surrounding anatomical matter 230 of surgical site "S." In particular, the edges 251 of surgical tool 250 as captured in images by image capture device 200, may be substituted for a test pattern 255a, 255b, and, as further described below, the edges 251 of surgical instrument 250, and particularly the contrast/difference between the luminance of surgical instrument 250 proximate edges 251 and the luminance of the background, e.g. surgical site "S," may be used as a pseudo test pattern 225c instead of actual test patterns 225a, 225b. While differences in contrast between any edges of surgical instrument 250 may be used to define a pseudo test pattern, in some embodiments slanted edges, e.g. straight edges that are at non-orthogonal angles as viewed by image capture device 200, are used. For example, analysis software may be used to look for and identify edges that are not substantially distant from, or off of, horizontal or vertical, e.g., between about 5° and 10° away.

Figure 4:
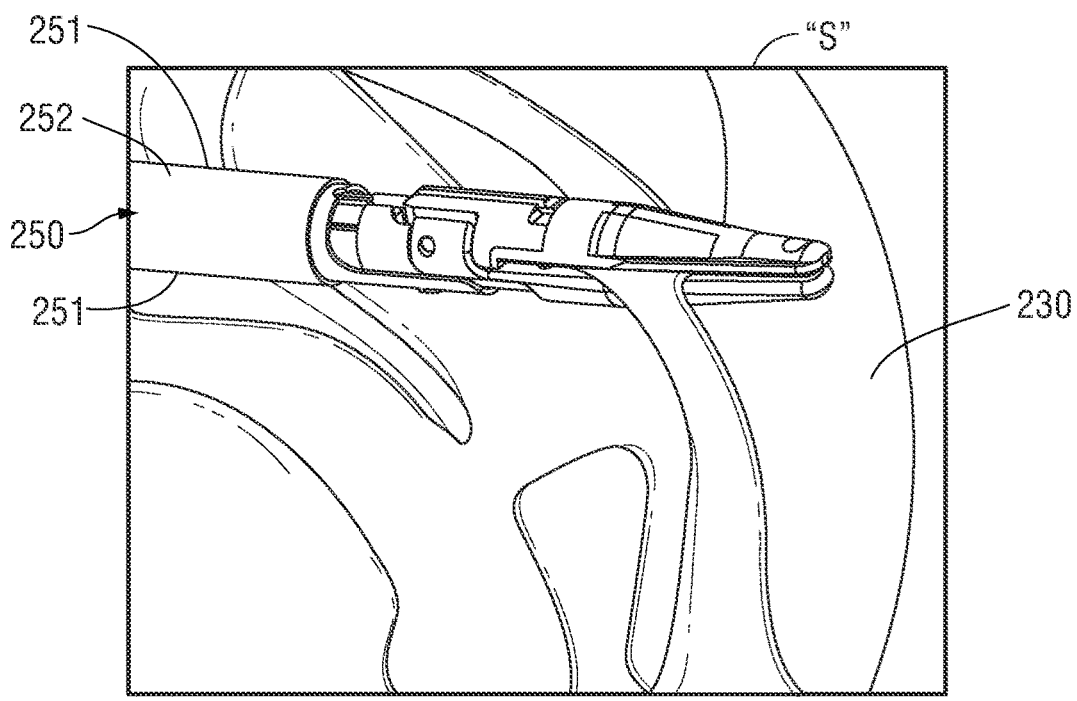
FIG. 4 is a test pattern formed by a difference in luminance between a surgical instrument and surrounding anatomical material, in accordance with an embodiment of the present disclosure.

FIG. 4 illustrates another view of surgical site "S," showing surgical instrument 250 placed within surgical site "S" and the surrounding anatomical material 230. A pseudo test pattern 255c is created from a section of the image of surgical site "S" including at least one edge 251 of surgical instrument 250. For example, a section an image of surgical site "S" including surgical instrument 250 and surrounding anatomical material 230 may be used to generate pseudo test pattern 255c, which may be based on the differences in luminance between surgical instrument 250, extending to edges 251, and surrounding anatomical material 230. For example, pseudo test pattern 255c may include a darker section contrasted with a brighter section on opposing side of edge 251 of surgical tool 250, thereby forming two zones of different and contrasted luminance created by surface 252 of surgical instrument 250 leading up to edges 251 of surgical instrument 250, and surrounding anatomical material 230. As will be appreciated by those skilled in the art, the brighter section and the darker section may respectively correspond to the surface 252 of surgical tool 250 and the surrounding anatomical material 230, and, depending on the type of surgical instrument 250 and/or image capture device 200, may be reversed in terms of which correspond to the brighter and darker sections.

Referring now to FIG. 5, an illustrative comparison is provided of an image of a test pattern captured during calibration of image capture device 200, and an image of the test pattern captured during a surgical procedure. For purpose of example, the illustrative comparison described below will refer to an image of test pattern 255b as disposed on surgical instrument 250 captured during calibration of image capture device 200, and an image of test pattern 255b' captured during the surgical procedure. However, those skilled in the art will recognize that other test patterns, such as described above, may also be used and/or substituted for test pattern 255b without departing from the scope of the present disclosure. The image of test pattern 255b is an image captured during calibration of image capture device 200, while the image of test pattern 255b' is the image received by image capture device 200 at some point during a surgical procedure. Due to occlusion of and/or anatomical material 230 coming into contact with lenses 210, 220, the image of test pattern 255b' is slightly blurred, or degraded, as compared to the image of test pattern 255b. As test patterns 255b, 255b' are viewed from left to right, each can be broken into groups of increasingly thinner width black bars and white bars. The contrast between black bars and white bars of test patterns 255b, 255b' is easily distinguished for all of area "X." However, within area "Y," it becomes increasingly difficult to distinguish the locations of black bars, white bars, and areas of transition of each.

In an embodiment, the image of test pattern 255b' is used to determine a value of a modulation transfer function ("MTF"). For example, the MTF is used to provide a measure of the transfer of contrast of test pattern 255b' and how well lenses 210, 220 of image capture device 200 reproduce (or transfer) the detail of test pattern 255b in a captured image. By obtaining an image of test pattern 255b or other test patterns (for example, test pattern 255a, pseudo test pattern 255c, and/or the like) during calibration of image capture device 200, baseline characteristics of the image of test pattern 255b or other test patterns can be determined. During use of image capture device 200, the ability of lenses 210, 220 of image capture device 200 to continue to reproduce (or transfer) the detail of the test pattern is determined by applying the MTF to the received image of the test pattern to yield one or more determined characteristics of the image of the test pattern. Over time, the determined characteristic(s) of the image of the test pattern may change due to degradation and/or occlusion of lenses 210, 220 of image capture device 200, for example, as shown in the image of test pattern 255b'. As described below with reference to FIG. 7, the baseline characteristics of the test pattern can be compared to the determined characteristic(s) of test pattern 255b' as image capture device 200 is used during a surgical procedure in order to determine when image degradation has occurred.

Figure 6:
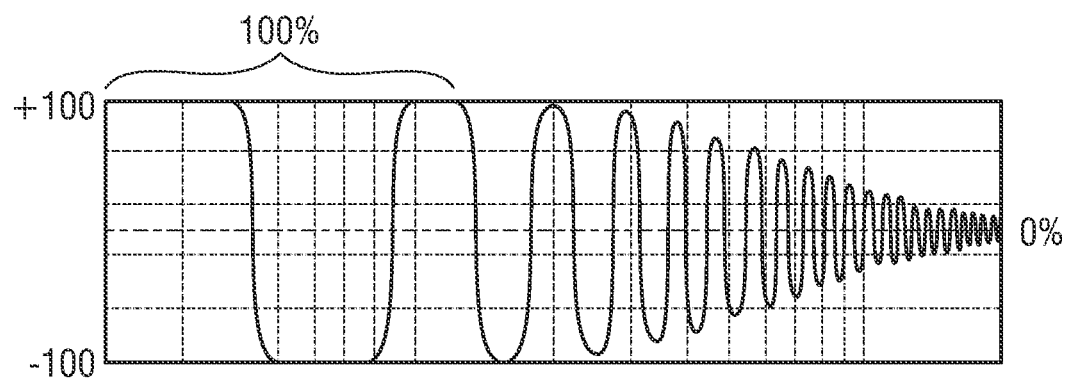
FIG. 6 is a modulation transfer function graph for the test pattern of FIG. 5, in accordance with the present disclosure.

In order to calculate the MTF for both the baseline characteristics of the test pattern and determined characteristic(s) of the test pattern, processor 32 is used to differentiate the black bars and white bars of test pattern 255b, or in the case of pseudo test pattern 255c, the darker sections and the brighter sections of the captured image proximate edges 251 of surgical instrument 250. Based on the differences between the black bars and white bars, or darker sections and brighter sections, a sinusoidal graph can be plotted. Turning now to FIG. 6, a graph of the contrast between black bars and white bars of test pattern 255b' of FIG. 5 is illustrated. The graph of FIG. 6 is used to calculate the MTF of test patterns 255b'. In some embodiments, such as depicted in the graph of FIG. 6, an amplitude of 100 is assigned to areas containing black bars and an amplitude of −100 is assigned for areas containing white bars. As test pattern 255b transitions between black bars and white bars the plot of the graph increases or decreases between the amplitude of −100 and 100.

Additionally, as the widths of the black bars and white bars of test pattern 255b' decrease, the ability of processor 32 to continue to differentiate between black bars and white bars may likewise decrease. As such, the peak amplitudes of the graph may no longer approach peak amplitudes of −100 and 100 such that, eventually, the width of the black bars and white bars becomes so thin that processor 32 can no longer distinguish the black bars from white bars of test pattern 225b' and the peak amplitude settles at 0. In some embodiments, a value of 100% may be assigned where the peak amplitude is between −100 and 100 and a value of 0% may be assigned where the peak amplitudes settles at 0. For peak amplitudes between −100 and 100, a corresponding percentage between 100% and 0% can be assigned. The MTF is typically expressed as a percentage of the distinguishable contrast between black bars and white bars based on the line widths per picture height (LW/PH). Thus, as the line widths (width of black bars and white bars) of test pattern 255b' become increasingly thinner, the percentage representing the contrast between the black and white bars decreases.

By assigning a value to the groups of increasingly thinner widths of black bars and white bars in the form of the LW/PH, the MTF percentage may correspond to the LW/PH. For example, if a portion of the graph of FIG. 6 ranges between peak amplitudes of 100 and −100 for a LW/PH as small as 100 mm, the MTF is 100% at 100 mm. If another portion of the graph of FIG. 6 ranges between peak amplitudes of 50 and −50 for the LW/PH at 50 mm, the MTF is 50% at 50 mm. These values of the MTF are determined by processor 32 and stored in memory 35.

In further embodiments, the MTF percentages may be converted from percentages ranging between 0% to 100% to corresponding values ranging between 0 and 1, wherein 0 corresponds to processor 32 being incapable of distinguishing black bars from white bars, and 1 corresponds to processor 32 being able to completely distinguish the black bars from white bars. It is further contemplated that processor 32 is capable of determining the MTF of test pattern 255b' as it is received by way of each of right-eye lens 210 and left-eye lens 220, independently. Thus, image degradation for images captured by way of each of right-eye lens 210 and left-eye lens 220 may be detected.

While the above description of FIGS. 5 and 6 refer to test pattern 255b as an example, similar determinations and calculations may be performed when pseudo test pattern 255c is substituted for test pattern 255b. For example, in embodiments, one or more slanted edges 251 of surgical instrument 250 may be used to calculate the MTF. In such embodiments, there may not be a test pattern 255a, 255b disposed on surgical instrument 250. Instead, the contrast between brighter sections and darker sections, corresponding to either the surface 252 proximate edge 251 of surgical instrument 250 or the surrounding anatomical material 230, respectively. Further information regarding computing the MTF based on a slanted edge 251 of surgical instrument 250 is described in *Slanted-Edge MTF for Digital Camera and Scanner Analysis*, by Peter D. Burns, Proc. IS&T 2000 PICS Conference, pg. 135-138 (2000), and Sharpness: What is it and how is it measured?, http://www.imatest.com/docs/sharpness (last visited Sep. 11, 2017), the entire contents of each of which are incorporated herein by reference.

Figure 7:
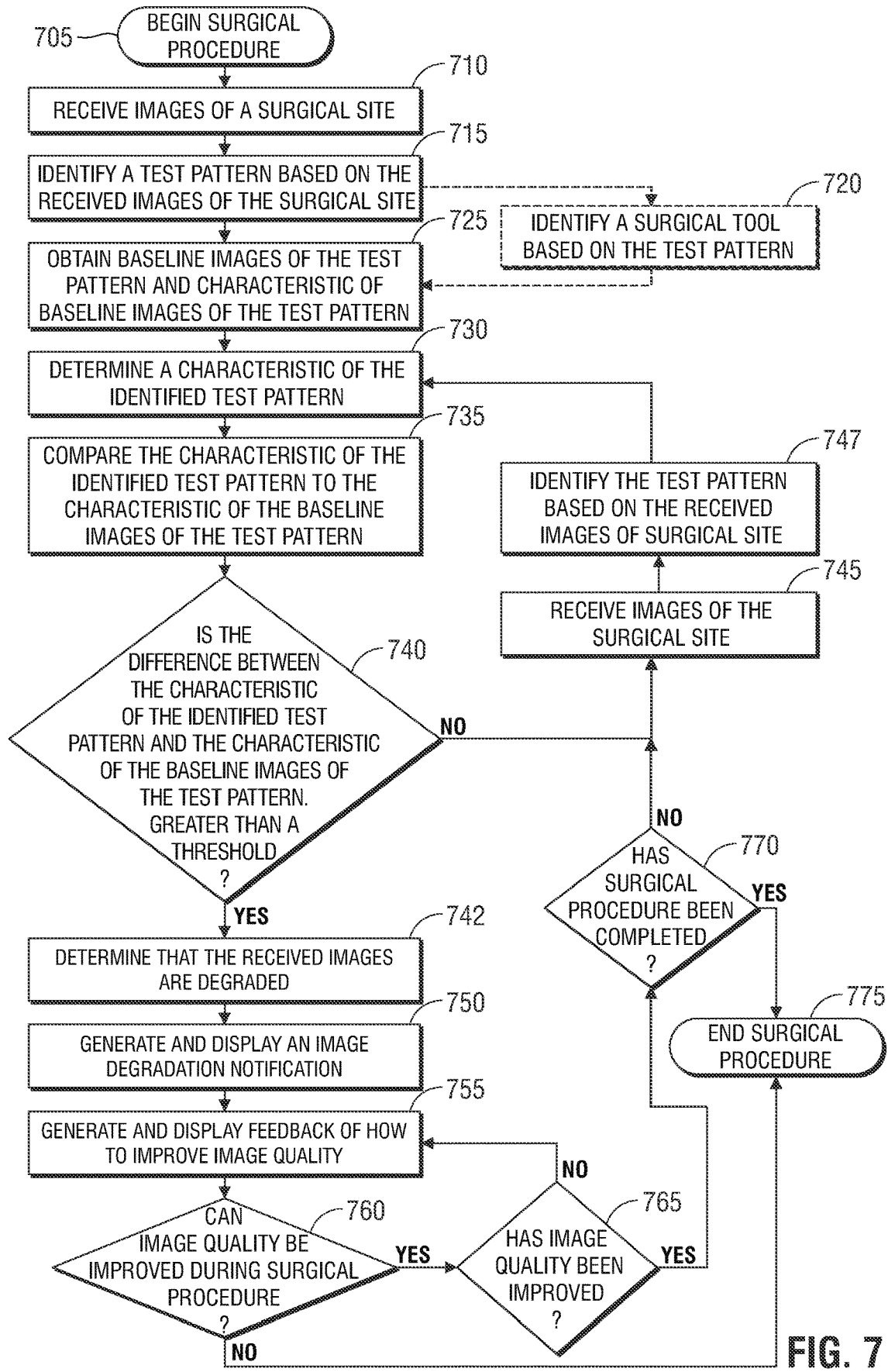
FIG. 7 is a flowchart illustrating an example method of detecting image degradation, in accordance with the present disclosure.

FIG. 7 is flowchart of a method 700 of detecting image degradation of images captured by image capture device 200 during a surgical procedure, in accordance with embodiments of the present disclosure. Method 700 may be implemented, at least in part, by processor 32 executing instructions stored in memory 35. Additionally, the particular sequence of steps shown in method 700 of FIG. 7 is provided by way of example and not limitation. Thus, the steps of method 700 may be executed in sequences other than the sequence shown in FIG. 7 without departing from the scope of the present disclosure. Further, some steps shown in method 700 of FIG. 7 may be concurrently executed with respect to one another instead of sequentially executed with respect to one another, and/or may be repeated or omitted without departing from the scope of the present disclosure.

Generally, prior to the execution of method 700, calibration of image capture device 200 will have been performed. For example, during a factory calibration process, image capture device 200 may receive, or the memory 32 may have stored therein, left-eye and right-eye images of one or more test patterns. The test patterns may be similar to test patterns 255a, 255b disposed on surface 252 of surgical device 250, or may be data related to the contrast between the edges of surgical device 250 and a surrounding environment, thereby generating a pseudo test pattern 255c. In another example, the calibration process may be performed at the start of a surgical procedure. In an embodiment in which images of the test patterns ("baseline images") are received by image capture device 200 during calibration, a pattern analysis function, such as the modulation transfer function (MTF), is applied to the test pattern to calculate output values. The output values may represent the sharpness or clarity of a transition across features making up the test pattern and may be expressed as line widths per picture height (LW/PH). The calculated output values may be included as one or more characteristics of the baseline images captured by the right-eye lens 210 and the left-eye lens 220 of the image capture device 200 ("baseline characteristics"), and can be stored in the memory 32 for later use, as will be described in detail below. Alternatively, these baseline characteristics may be known values that are stored in the memory 32. Additionally, during a calibration process, image capture device 200 may store the baseline characteristics of the test pattern in memory.

In any case, surgical system 10 is configured to permit the user to begin the surgical procedure within surgical site "S," at step 705. For example, in the case of a robotic surgical procedure, the user moves the gimbals 70 to thereby position image capture device 200 and surgical instrument 250 about surgical site "S". In some embodiments, the field of view of image capture device 200 may initially be aligned with surgical instrument 250 to enable image capture device 200 to capture images of surgical instrument 250, and particularly test patterns 255a, 255b, via right-eye lens 210 and left-eye lens 220, respectively. Alternatively, as will be appreciated by those skilled in the art, in non-robotic minimally-invasive surgical procedures, image capture device 200 and surgical instrument 250 may be positioned manually about surgical site "S."

Once suitably positioned, image capture device 200 captures images of surgical site "S," and transmits the captured images to controller 30 at step 710. In addition to tissue and surrounding anatomical material 230 on which the surgical procedure is being performed, the captured images show surgical instrument 250 as it is being manipulated by the user. The captured images may be stereoscopic images, that is, left-eye images and right-eye images.

After receiving the captured images from image capture device 200, processor 32 processes the captured images to identify a test pattern, at step 715. As described herein, it is contemplated that the test pattern may be a pattern disposed on surface 252 of surgical instrument 250 or a test pattern formed by the contrast been surgical instrument 250 and surrounding anatomical material 230 about a slanted edge 251 of surgical instrument 250. As noted above, examples of test patterns include but are not limited to test patterns 255a, 255b and pseudo test pattern 255c, and/or the like. In an embodiment, a suitable algorithm is applied to the left-eye images and the right-eye images of surgical site "S" to output a result, which is analyzed by processor 32 to detect a presence of the test pattern.

Optionally, in an embodiment where test pattern 255b is disposed on surgical instrument 250, at step 720, after identifying test pattern 255b', a determination is made as to whether test pattern 255b' matches a known test pattern. For example, a database of known test patterns may be stored in memory 35, for example, in a look-up table. The images of test pattern 255b' captured by image capture device 200 is compared with the known test pattern images stored in memory 35. In an embodiment, each of the known test patterns is associated with a different surgical instrument. As such, matching test pattern 255b' with the known test pattern further includes identifying the surgical instrument corresponding to the known test pattern. In an embodiment, the identification of the surgical instrument is provided to the user via display device 44 or through an audio device. For illustrative purposes and provided by way of example, pseudo test pattern 255c, that is, the slanted edges 251 of surgical instrument 250, is used as the exemplary test pattern for the remaining description of FIG. 7.

At step 725, the one or more baseline characteristics of the test pattern ("characteristic(s) of the baseline image of the test pattern"), generated and/or calculated during calibration, are obtained. In embodiments where the calibration process is not performed prior to the start of the surgical procedure, the calibration process may be performed at step 725. In other embodiments, as noted above, the characteristic(s) of the baseline images of the test pattern may be stored in memory 35. In such embodiments, the corresponding characteristic(s) of the baseline image of the test pattern are retrieved from a lookup table and/or database stored in memory 35.

At step 730, the image of pseudo test pattern 255c received at step 715 is analyzed and one or more characteristics are determined from the images of pseudo test pattern 255c. In an embodiment, a MTF is calculated for the images of pseudo test pattern 255c in order to determine the characteristics of the images of pseudo test pattern 255c. The determined characteristic(s) of the images of pseudo test pattern 255c may be in the form of a percentage at LW/PH. For example, at step 730, the MTF may yield values of 100% at 105 mm and 45% at 50 mm. In other embodiments, various other types of analysis functions may be applied to the images of pseudo test pattern 255c. In any case, step 730 is continuously reiterated, so that changes in the determined characteristic(s) of the images of pseudo test pattern 255c may be detected from the images of pseudo test pattern 255c over time.

In step 735, the determined characteristic(s) of the images of pseudo test pattern 255c are compared to the one or more characteristics of the baseline images of pseudo test pattern 255c. In one embodiment, it is contemplated that either the percentage or the LW/PH are selected at a specific value for the characteristic(s) of the baseline images of pseudo test pattern 255c to be compared with percentages or LW/PH of the determined characteristic(s) of images of pseudo test pattern 255c. For example, if the LW/PH is selected for the characteristic(s) of the baseline images of pseudo test pattern 255c at a specific value of 50 mm and the corresponding percentage is 50% (thus yielding a MTF graph amplitude ranging from 50 to −50 at LW/PH of 50 mm), as described above in the description of FIG. 6, then at step 735 the determined characteristic(s) of images of pseudo test pattern 255c at LW/PH of 55 m (45% at 50 mm, as described in step 30) are compared to 50% at 50 mm. Thus, using the examples above, the comparison between the characteristic(s) of the baseline images of pseudo test pattern 255c and the determined characteristic(s) of pseudo test pattern 255c yields a 5% difference.

In an embodiment, at step 740, a determination is made as to whether the difference between the characteristic(s) of the baseline images of pseudo test pattern 255c and the determined characteristic(s) of the images of pseudo test pattern 255c is greater than a predetermined threshold. The predetermined threshold is a percentage decrease between the characteristic(s) of the baseline images of pseudo test pattern 255c and the determined characteristic(s) of pseudo test pattern 255c. For example, a predetermined threshold of the modulation function may translate to a decrease of a 15% of line widths per picture height (LW/PH), which may indicate image marrying from material on the lens of one or both images. If the difference is not greater than a predetermined threshold ("NO" at step 740), method 700 proceeds to step 745, where new images of surgical site "S" are received. Next, at step 747, similar to step 715, the new images of surgical site "S" are processed to identify pseudo test pattern 255c. Following step 747, method 700 returns to step 730 where the received images of pseudo test pattern 255c are analyzed by processor 32 and one or more characteristics of the images of pseudo test pattern 255c are determined.

It is contemplated that steps 730 through step 740 and returning to step 730 may be performed iteratively and repeated at regular intervals. In one embodiment, it is contemplated that processor 32 will proceed from steps 730 through step 740 returning to step 730 processing newly received images of surgical site "S" at 60 Hz, possibly 30 Hz, and even as low as 10 Hz. Thus, relatively frequently, new images of surgical site "S" is received, processed, and a determination made as to whether the difference between the characteristic(s) of the baseline image of pseudo test pattern 255c and the determined characteristic(s) of the images of pseudo test pattern 255c, is greater than a predetermined threshold. In other embodiments, based on the surgical procedure, the intervals from steps 730 through step 740 returning to step 730 may be shortened in order to increase the frequency of the determination of image degradation, for example, every half, quarter, or one-tenth of a second.

In a further embodiment, a determination is made as to whether a trend is detected from the differences determined at step 735. It is contemplated that the differences from step 735 are stored in memory 35, and the data is monitored to determine the trend. For example, processor 32 may determine that image degradation has likely occurred due to tissue occluding one or both of lenses 210, 220, where image degradation occurs rapidly following a small number of passes from steps 730 through 740 and returning to step 730. Alternatively, processor 32 may determine that image degradation has occurred due to a gradual build-up of fluid or other anatomical material where image degradation occurs more slowly.

If, at step 740, it is determined that the difference between the characteristic(s) of the baseline images of pseudo test pattern 255c and the determined characteristic(s) of the images of pseudo test pattern 255c is greater than a predetermined threshold ("YES" at step 740), method 700 proceeds to step 742. At step 742, a determination is made as to whether image degradation has occurred, based on the result of the determination at step 740. For example, image degradation may include the images being distorted, out of focus, partially or wholly occluded, and/or a mismatch between the images captured by left-eye lens 210 and right-eye lens 220, thereby causing a stereoscopic visual distortion even if the images, when viewed separately, do not appear distorted. Thereafter, method 700 proceeds to step 750, where a notification is generated and provided to the user indicating that image degradation may have occurred. The notification may be displayed, for example, via display device 44 or portable display device 45 of user interface 40, and/or be provided audibly or tactilely via gimbals 70.

Following step 750, method 700 proceeds to step 755 where feedback is provided to the user indicating how image quality may be improved. For example, the feedback provided may be in the form of a notification via display device 44 or portable display device 45, that the user should remove and clean one or both of lenses 210, 220 in order to improve image quality. After feedback is provided indicating how to improve image quality at step 755, the method 700 proceeds to step 760 where it is determined whether the image quality can be improved during the surgical procedure. For example, it may be determined whether image capture device 200 needs to be removed from surgical site "S" and cleaned, or be replaced. Those skilled in the art will envision various other actions that may be taken to improve the image quality of images captured by image capture device 200, and thus, for purpose of brevity, all such alternative actions will not be described here. If it is determined at step 760 that the image quality cannot be improved during the surgical procedure ("NO" at step 760), the method 700 proceeds to step 775 where the surgical procedure ends. Alternatively, if it is determined at step 760 that the image quality can be improved during the surgical procedure ("YES" at step 760), the method 700 proceeds to step 765.

At step 765 it is determined whether the image quality has been improved. For example, the processes described above with reference to steps 745, 747, 730, 735, and 740 may be repeated to determine whether the image quality of images captured by image capture device 200 has been improved. If it is determined at step 765 that the image quality has not been improved ("NO" at step 765), processing returns to step 755. Alternatively, if it is determined at step 765 that the image quality has been improved ("YES" at step 765), the method 700 proceeds to step 770.

At step 770 it is determined whether the surgical procedure has been completed. For example, it may be determined whether the user has provided an instruction and/or indication that the surgical procedure has been completed. If it is determined at step 770 that the surgical procedure has not been completed ("NO" at step 770), processing returns to step 745. Alternatively, if it is determined at step 770 that the surgical procedure has been completed ("YES" at step 770), processing ends.

Referring back to the computer-readable media of FIG. 1, memory 35 includes any non-transitory computer-readable storage media for storing data and/or software that is executable by processor 32 and which controls the operation of controller 30. In an embodiment, memory 35 may include one or more solid-state storage devices such as flash memory chips. Alternatively or in addition to the one or more solid-state storage devices, memory 35 may include one or more mass storage devices connected to processor 32 through a mass storage controller (not shown) and a communications bus (not shown). Although the description of computer-readable media contained herein refers to a solid-state storage, it should be appreciated by those skilled in the art that computer-readable storage media can be any available media that can be accessed by processor 32. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by controller 30. Further aspects of the system and method are described in U.S. Pat. No. 8,828,023 entitled "MEDICAL WORKSTATION," filed on Nov. 3, 2011, the entire contents of all of which are hereby incorporated by reference.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to employ the present disclosure in virtually any appropriately detailed structure.

What is claimed is:

1. A method for detecting image degradation during a surgical procedure, the method comprising:
   receiving an image of a surgical instrument, the image of the surgical instrument including a test pattern disposed on an outer surface of the surgical instrument, wherein the test pattern includes increasingly thinner alternating dark bars and light bars;
   obtaining a characteristic of the test pattern;
   processing the image to identify the test pattern, which is captured in the received image and which is disposed on the outer surface of the surgical instrument;
   determining a characteristic of the identified test pattern in the image of the surgical instrument;
   calculating a difference between the determined characteristic and the obtained characteristic; and
   generating an image degradation notification based on the difference.

2. The method according to claim 1, further comprising capturing the image of the surgical instrument by an image capture device.

3. The method according to claim 2, wherein the image capture device is a stereoscopic endoscope including a left-eye lens and a right-eye lens.

4. The method according to claim 1, further comprising obtaining the characteristic of the test pattern based on a baseline image of the test pattern.

5. The method according to claim 1, wherein the characteristic of the test pattern is obtained from a lookup table or a database.

6. The method according to claim 1, wherein the test pattern corresponds to a type of the surgical instrument.

7. The method according to claim 1, further comprising determining the characteristic of the identified test pattern based on a modulation transfer function (MTF) on the test pattern.

8. The method according to claim 7, wherein the MTF is a percentage of contrast between the dark bars and the light bars.

9. The method according to claim 1, further comprising periodically receiving another image of the surgical instrument at a predetermined interval.

10. A system for detecting image degradation during a surgical procedure, the system comprising:
   a surgical instrument;
   an image capture device configured to capture an image of the surgical instrument, the image of the surgical instrument including a test pattern disposed on an outer surface of the surgical instrument, wherein the test pattern includes increasingly thinner alternating dark bars and light bars;
   at least one processor coupled to the image capture device; and
   a memory coupled to the at least one processor and having instructions stored thereon, that, when executed by the at least one processor, cause the at least one processor to:
      obtain a characteristic of the test pattern;
      process the image to identify the test pattern, which is captured in the image and which is disposed on the outer surface of the surgical instrument;
      determine a characteristic of the identified test pattern in the image of the surgical instrument;
      calculate a difference between the determined characteristic and the obtained characteristic; and
      generate an image degradation notification based on the difference.

11. The system according to claim 10, wherein the image capture device is a stereoscopic endoscope including a left-eye lens and a right-eye lens.

12. The system according to claim 10, wherein the characteristic of the test pattern is obtained based on a baseline image of the test pattern.

13. The system according to claim 10, wherein the characteristic of the test pattern is obtained from a lookup table or a database.

14. The system according to claim 10, wherein the test pattern corresponds to a type of the surgical instrument.

15. The system according to claim 10, wherein the characteristic of the identified test pattern is determined based on a modulation transfer function (MTF) on the test pattern.

16. The system according to claim 15, wherein the MTF is a percentage of contrast between the dark bars and the light bars.

17. The system according to claim 10, further comprising wherein the at least one processor periodically receiving another image of the surgical instrument at a predetermined interval.

18. A non-transitory computer-readable medium storing instructions that, when executed by a processor, cause the processor to:
   receive an image of a surgical instrument;
   obtain a characteristic of a test pattern disposed on an outer surface of the surgical instrument, wherein the test pattern includes increasingly thinner alternating dark bars and light bars;
   process the image to identify the test pattern, which is captured in the received image and which is disposed on the outer surface of the surgical instrument;
   determine a characteristic of the identified test pattern in the image of the surgical instrument;
   calculate a difference between the determined characteristic and the obtained characteristic;
   obtain baseline images of one or more straight outer edges of the surgical instrument;
   compare a characteristic of one or more straight outer edges of the surgical instrument in the images to a characteristic of the one or more straight outer edges of the surgical instrument in the baseline images, the images of the surgical instrument being received subsequent to the obtaining of the baseline images and being received while the surgical instrument is disposed at a surgical site in a patient;
   determine whether the images of the surgical instrument are degraded, based on the comparison of the characteristic of one or more straight outer edges of the surgical instrument in the images and the characteristic of the one or more straight outer edges of the surgical instrument in the baseline images; and
   generate an image degradation notification based on the difference between the determined characteristic and the obtained characteristic, and in response to a determination that the images of the surgical instrument are degraded.

19. The non-transitory computer-readable medium according to claim 18, wherein the characteristic of the test pattern is obtained from a lookup table or a database.

20. The non-transitory computer-readable medium according to claim 18, wherein the test pattern corresponds to a type of the surgical instrument.

* * * * *